United States Patent [19]

Williams et al.

[11] Patent Number: 5,186,972

[45] Date of Patent: Feb. 16, 1993

[54] METHOD FOR LUBRICATING ARTICLES

[75] Inventors: Joel L. Williams, Cary; Thomas A. Shepard, Raleigh, both of N.C.

[73] Assignee: Becton, Dickinson and Company, Franklin Lakes, N.J.

[21] Appl. No.: 710,984

[22] Filed: Jun. 6, 1991

[51] Int. Cl.$^5$ .......................... A01N 1/02; B05D 3/00
[52] U.S. Cl. .......................................... 427/2; 427/230; 427/398.1; 427/421; 427/430.1; 427/435
[58] Field of Search ................ 427/398.1, 2, 230, 421, 427/430.1, 435

[56] References Cited

U.S. PATENT DOCUMENTS

| | | | |
|---|---|---|---|
| 2,795,278 | 6/1957 | Battle | 166/1 |
| 3,574,673 | 4/1971 | Schweiger | 117/132 |
| 3,855,137 | 12/1974 | Whitney | 252/62.52 |
| 4,371,645 | 2/1983 | Mahaffey, Jr. | 524/108 |
| 4,664,657 | 5/1987 | Williamitis et al. | 604/265 |
| 4,720,521 | 1/1989 | Spielvogel et al. | 524/862 |
| 4,767,414 | 8/1989 | Williams et al. | 604/230 |
| 4,808,650 | 2/1989 | Titus et al. | 524/108 |
| 4,845,137 | 7/1989 | Williams et al. | 524/108 |

*Primary Examiner*—Bernard Pianalto
*Attorney, Agent, or Firm*—Richard E. Brown

[57] ABSTRACT

In a method for lubricating articles, a liquid composition including a gelling agent dissolved in a lubricant is applied to the surface of an article and caused to gel on the article. Gelling may be induced by applying the liquid composition to an article at a temperature below the gelling temperature of the composition, or the article coated with the liquid composition may be cooled to induce gelling.

15 Claims, No Drawings

METHOD FOR LUBRICATING ARTICLES

BACKGROUND OF THE INVENTION

1. Field of the Invention

This invention relates to medical articles and more particularly relates to a solventless method for lubricating articles.

2. Background of the Invention

Many occasions arise when it is necessary to puncture the skin with a metal device, generally of stainless steel, having a sharp point or edge. Representative of such devices are syringe needles, surgical blades, lancets, cannulas, catheter insertion devices and the like. In other cases, a cutting edge, such as a razor blade, is advanced across a skin surface.

When such a device is advanced across the skin or inserted through the skin, the skin is stretched and a certain amount of pain is experienced. It has been common practice for many years to lubricate the device to minimize pain.

Noncuring, nonpolar silicones, such as the DC ®360 series of medical grade polydimethylsiloxanes (PDMS) available from Dow Corning Co. have been used. These products have the disadvantage of ease of wipe-away or migration from the surface to which they have been applied. Another problem with these lubricants is adhesion which develops over time when metal to plastic or two plastic surfaces are engaged by an interference fit. For plastic syringe barrels and associated plunger, Williams et al., in U.S. Pat. No. 4,767,414, discloses that plasma treatment of one of the surfaces and the oil overcomes adhesion. For a catheter-cannula assembly, Williamitis et al. discloses in U.S. Pat. No. 4,664,657 that adhesion can be mitigated if the PDMS is of high viscosity.

The problem of wipe-away is particularly severe when metal surfaces are lubricated with noncuring PDMS. For example, in the case of a hypodermic needle coated with PDMS, the coating may be substantially removed due to frictional wiping forces during penetration of the skin and vein, making subsequent removal of the needle difficult and painful to the patient. Migration during storage and inadvertent removal during processing is also a concern.

For these reasons, commercial syringe needles are usually coated with proprietary silicone-based lubricants applied by wiping, spraying or dip coating from solvents such as FREON ™. These lubricants reduce maximum penetration force by about 20% and usually contain silicone oil plus a room temperature vulcanizable silicone which serves as a matrix to prevent removal of lubricant during penetration. The matrix only minimizes the lubricant removal and penetration forces approach that of a dry needle after 2 to 3 sequential penetrations. Also, the standard commercial systems require long cure times on the order of one to several days. Exemplary of these lubricating systems is the disclosure in U.S. Pat. No. 3,574,673 to Schweiger of friction reducing coatings on blades consisting of alkylamine-modified methoxysiloxanes which undergo moisture curing at ambient temperature.

In similar fashion, U.S. Pat. No. 4,720,521 to Spielvogel discloses a noncuring lubricating PDMS occluded in a mixture of at least three curing silicones which adhere to a metal surface.

Copending application Ser. No. 628,139 of common assignee herewith discloses metal articles having a coating of a polar noncuring silicone lubricant.

Copending application Ser. No. 640,714 of common assignee herewith discloses a composition which includes an aqueous emulsion of a noncuring polar silicone lubricant and a metal article having a coating of the composition thereon.

U.S. Pat. No. 5,041,310 discloses a process for coating polymeric particles with an additive composition which includes a mobilizing oil, a radiation stabilizer and a gelling agent.

While the above disclosures all teach improved compositions and methods for lubrication, there remains a need for a composition and method which overcomes migration and wipe-away problems without a curing step using simple and inexpensive nonpolar silicones.

SUMMARY OF THE INVENTION

In a method for lubricating an article, a composition including a gelling agent dissolved in a lubricating oil is coated onto a surface of the article at a temperature above the gelling temperature of the composition. The coated article is cooled below the gelling temperature to cause the composition to gel on the article surface. Alternatively, the liquid composition may be coated onto the article at a temperature below the gelling temperature so that gellation occurs on contact.

Preferred lubricating oils are silicones, preferably noncuring, nonpolar polydialkylsiloxanes. Preferred gelling agents are ethers of polyhydroxy compounds, most preferably ethers of sorbitol.

The invention includes a composition consisting substantially of a solution of the gelling agent in the lubricant.

As is well-known in the art, oils of low viscosity are generally better lubricants than oils of higher viscosity. However, it is also well-known that lower viscosity oils have a greater tendency to creep or migrate, and are of course more subject to wipe-away. By the method of the invention, the preferred lubricating oil is of low to intermediate viscosity and is coated onto an article surface as a thin layer of substantially solid gel.

Even though the oil is of low viscosity, migration and wipe-away is greatly reduced because of the substantially solid nature of the gel. Further, the lubricating effect of the gelled oil is not compromised because the gel thins by thixotropy when subjected to any shear force, such as force applied to cause needle penetration.

Accordingly, when a needle lubricated in accordance with the invention is inserted through the skin, the lubricant is not wiped away to form a pool on the skin surface but instead remains adherent and is thus available as a lubricant when the needles is retracted. In contrast, a metal needle lubricated with a conventional lubricant suffers significant beading and wipe-away even when adhered by a curing step so that little is left for retraction. Significant pain is experienced by the patient due to the friction between the substantially bare needle and the skin. Similarly, other cutting devices, such as surgical blades, cannulas and lancets may be used with less pain for the patient due to the enhanced retention of the gelled lubricant.

A further advantage of the invention is provision of a method for lubricating a metal or plastic article which eliminates the need for toxic curing agents used with most conventional lubricants. The invention also avoids the toxic solvents used in conventional dip coating, in particular, use of ozone-damaging fluorocarbon solvents, and thus has environmental advantages over conventional methods for lubricating.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the present invention, articles are lubricated with a composition which includes a gelling agent dissolved in a lubricant.

Preferred articles are metal articles. While the invention contemplates lubrication of articles of any metal, preferably steel, the most preferred articles are of stainless steel.

Representative nonlimiting metal articles contemplated to be lubricated with the polar lubricant of the invention are scalpels, razor blades and surgical blades, hypodermic needles, lancets and any metal catheter insertion device.

Thus, in one preferred embodiment of the invention, the metal article includes a cutting edge, such as a surgical blade, having the composition coated thereon. Another preferred embodiment is a metal article having a cutting point for puncture of a membrane, preferably skin, such as a cannula or needle having the composition coated thereon. The most preferred article is a syringe needle coated with the composition.

It is not intended to limit the invention to metal articles. In another preferred embodiment, the invention includes a plastic article having a surface contemplated to function in a sliding relationship with another surface. For this embodiment of the invention, suitable surfaces are of natural or synthetic rubber or preferably of thermoplastic or thermoset polymers such as polyethylene, polypropylene, polystyrene, polytetrafluoroethylene and the like. A particularly preferred article is a polymeric syringe stopper which slides within a polymeric syringe barrel lubricated with the composition of the invention.

The invention contemplates any gelling agent-lubricant combination in which the gelling agent is soluble in the lubricant, and, after application to the article surface as a homogeneous liquid, subsequently forms a substantially nonmobile lubricating gel on the article. Suitable lubricants are hydrocarbon oils such as vegetable oil, corn oil, peanut oil, mineral oil and synthetic lubricating oils such as a silicone and a phthalate oil, as, for example, butyl phthalate. Mixtures of lubricating oils may be used.

A preferred class of lubricants are noncuring, nonpolar polydialkylsiloxanes of general structure I having trialkylsiloxy terminal groups.

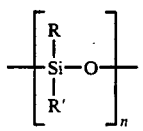

In structure I, R and R' may be independently a lower alkyl of 1 to 20 carbon atoms, preferably 1 to 8 carbon atoms, and n may be an integer from 1 to 2,000, preferably 1 to 800. The preferred lubricants of structure I have viscosities of from about 10 to 100,000 centistokes. These products are well-known and a wide variety of products ranging in viscosity from 0.65 to 2,500,000 centistokes are commercially available from Petrarch Systems.

Particularly preferred nonpolar lubricants are the DC®360 medical grade polydimethylsiloxanes ranging in viscosity from 20 to 60,000 commercially available from Dow Corning Corp., Midland, Mich. The most preferred nonpolar lubricants are DC®360 fluids of viscosity about 20 to 12,500 centistokes.

A wide range of organic gelling agents may be used in the composition. Suitable gelling agents are salts of carboxylic acids such as p-tertiary butylbenzoic acid. Preferred acid salts are metal salts of long chain fatty acids such as stearic acid and 12-hydroxy stearic acid. The metal ion of these salts may be an alkali metal or an alkaline earth metal.

Preferred gelling agents in accordance with the invention are ethers of polyhydroxy compounds such as xylitol, mannitol, pentaerythritol and sorbitol. Particularly preferred gelling agents are dibenzyl sorbitol, dibenzylidene sorbitol (DBS) and ring substituted derivatives thereof such as 4,4'-dimethyl dibenzylidene sorbitol (MDBS), 4,4'-dichlorodibenzylidene sorbitol (CDBS) and 4,4'-bis(methylthio)dibenzylidene sorbitol (MTDBS). As known in the art, these compounds are clarifying agents for polymeric compositions. Clarifying dibenzylidene sorbitols are disclosed in U.S. Pat. No. 4,371,645 to Mahaffey and U.S. Pat. Nos. 4,808,650 and 4,845,137 to Titus et al.

A mixture of gelling agent and the lubricant may be heated at a temperature above the gelling temperature of the solution until a homogeneous composition is obtained. A concentration of about 0.01 to 2.0% by weight of the gelling agent may be used. It has been found, for example, that sorbitol derivatives at a concentration of less than 1% are sufficient to gel silicone oils.

Any suitable temperature above the gelling temperature may be used to dissolve the gelling agent, preferably about 100° to 300°, most preferably about 150° to 250° C. The temperature of gelling depends on the nature of the gelling agent and lubricant and the concentration of the gelling agent.

Coating of the article with the composition containing the gelling agent may be carried out by any convenient technique. The composition, above its gelling temperature, may be wiped or sprayed onto the article at a temperature such that the article is coated with the liquid composition. Other suitable procedures are conventional roll coating or printing. Preferably the article may be coated by dipping into the liquid composition. On cooling the coated article below the gelling temperature of the composition, the gelling agent causes the composition to solidify on the article into a uniform solid lubricious coating which does not migrate. Alternatively, the liquid composition may be sprayed onto articles which have been cooled below the gelling temperature such that the liquid composition gels immediately on contacting the cooled article. In still another coating process, the composition may be cooled until it gels and the article added and tumbled with the gelled composition to effect coating.

The thickness of the coating may be about 0.5 to 50μ depending on factors such as the viscosity of the composition, the method of applying, and, for dip application, the rate of withdrawal of the article from the composition. Preferably the rate of withdrawal is about 5 to 100, most preferably about 50 mm/min.

Lubricity of needles coated by the method of the invention may be tested by measuring the force required for penetration of gray vial rubber stoppers using the Instron Model 1122 Universal Testing Machine. Syringe needles coated with representative gelled compositions of the invention give reductions in penetration force of about 40% as given in the examples. For comparison, force reductions of about 20% are achieved under the same conditions using a proprietary commercial lubricant of a curing polysiloxane.

The following examples are provided to further illustrate the invention but are not to be considered as limitative of the invention.

EXAMPLE I

DBS at 0.35% by weight was added to 350 centistoke silicone oil and heated to 200° C. to dissolve the DBS. The temperature was adjusted to 180° C., and a dry 22 gauge stainless steel needle was dipped vertically and withdrawn at a rate of 50 mm/min. The needle was cooled to cause the coating to gel and allowed to equilibrate at 25° C. for 2 hours. Using the Instron, penetration testing was performed through gray vial rubber stoppers. Five samples were tested and found to have an average penetration force of 431 gm (s.d.=24 gm). An unlubricated needle had a penetration force of 714 gr (s.d.=74 gm). The relative penetration force of 0.60 may be calculated by the equation $$F_{relative} = \frac{431 \text{ gm}}{714 \text{ gm}}$$

and is a 40% improvement over the dry needle.

In the same way, the following results were obtained using DBS and 350 centistoke silicone oil:

| % of gelling agent | dip rate mm/min | penetration force (gm) | % improvement over control |
|---|---|---|---|
| 0.50 | 50 | 408 | 43 |
| 0.35 | 500 | 414 | 42 |
| 0.50 | 500 | 440 | 38 |
| 0.50 | 200 | 443 | 38 |
| 0.35 | 200 | 439 | 39 |

EXAMPLE II

A 22 gauge dry stainless steel needle was dipped in 350 centistoke silicone oil at 50 mm/min and suspended in a vertical position at 25° C. with the tip down.

In a separate experiment, an identical needle was gel coated with a 350 centistoke silicone oil containing 0.5% DBS by the procedure of Example I and suspended vertically with the tip down. The needle without DBS as a gelling agent lost 16.1 mg in 14 days while the DBS gelled sample lost only 1.1 mg in 14 days.

This example demonstrates the minimization of lubricant migration brought about by the gelling agent.

EXAMPLE III

In separate experiments, 0.5% DBS, MDBS and CDBS were added separately to corn oil, butylphthalate oil, mineral oil and silicone oil. The temperature was adjusted as in Example I, the needles were dipped and the penetration forces measured as summarized below:

| OIL | VISCOSITY (cS) | % GELLING AGENT | PENETRATION FORCE (gm) | % IMPROVEMENT OVER CONTROL |
|---|---|---|---|---|
| Corn Oil | 10 | 0.5% DBS | 609 | 15 |
|  |  | 0.5% MDBS | 635 | 11 |
|  |  | 0.5% CDBS | 649 | 9 |
| Butyl Phthalate | 25 | 0.5% DBS | 601 | 16 |
|  |  | 0.5% MDBS | 664 | 7 |
|  |  | 0.5% CDBS | 618 | 13 |
| Mineral Oil | 25 | 0.5% DBS | 697 | 6 |
|  |  | 0.5% MDBS | 648 | 9 |
|  |  | 0.5% CDBS | 633 | 11 |
| Silicone Oil | 20 | 0.5% DBS | 555 | 22 |
|  |  | 0.5% MDBS | 580 | 19 |
|  |  | 0.5% CDBS | 567 | 21 |

EXAMPLE IV

A gel of DBS, 0.25% in 1,000 cS silicone oil was prepared and applied to a needle as in Example I. The gel lubricated needle was tested as in Example I and found to have a relative penetration force of 0.589. The percent improvement over the dry control was 41%.

EXAMPLE V

A gel of DBS, 0.25% in 12,500 cS silicone oil was prepared and applied to a needle as in Example I. The gel lubricated needle was tested as in Example I and found to have a relative penetration force of 0.583. The percent improvement over the dry control was 42%.

EXAMPLE VI

MDBS at 0.25% by weight was added to 1,000 cS silicone oil and heated to 180° C. to dissolve the gelling agent. The solution was applied to the inside of a 10 cc polypropylene syringe barrel and gelled by cooling. A control 1,000 cS silicone oil was added to a separate dry syringe barrel without the MDBS gelling agent.

The forces required to move the plunger were measured on an Instron testing machine at a constant speed of 200 mm/min. The results are given in the table below for samples with/without gelling agent, commercial syringe and dry syringe.

| SAMPLE | % MDBS | SILICONE OIL | PLUNGER* FORCE (gm) |
|---|---|---|---|
| Dry | — | — | >1,000 |
| Commercial (10cc) | — | 12,500 | 260 |
| No gel agent | 0 | 1,000 | 140 |
| With gel agent | 0.25% | 1,000 | 180 |

*Avg of 2 syringes

This example demonstrates that excellent plunger forces can be achieved with lower viscosity silicone oils, and the gelation will prevent migration of the oil.

What is claimed is:
1. A method for lubricating an article comprising:
   a) preparing a lubricating composition by dissolving a gelling agent selected from the group consisting of an ether of a polyhydroxy compound and a fatty acid salt in a lubricant at a temperature above the gelling temperature of said composition so that said composition is liquid;

b) applying a coating of the liquid composition to the surface of an article to be lubricated; and c) cooling the coated article below said gelling temperature whereby said liquid composition gels on said surface.

2. The method of claim 1 wherein said article is selected from the group consisting of a metal article and a plastic article.

3. The method of claim 2 wherein said metal article is a needle.

4. The method of claim 2 wherein said metal article is a blade.

5. The method of claim 2 wherein said plastic article is a syringe barrel.

6. The method of claim 1 wherein said applying step is performed by spraying said composition onto said article.

7. The method of claim 1 wherein said polyhydroxy compound is selected from the group consisting of xylitol, sorbitol, pentaerythritol and mannitol.

8. The method of claim 7 wherein said ether of sorbitol is selected from the group consisting of dibenzyl sorbitol, dibenzylidene sorbitol and ring substituted derivatives thereof.

9. The method of claim 1 wherein said lubricant is selected from the group consisting of a hydrocarbon oil, a silicone oil and a phthalate oil.

10. The method of claim 9 wherein said silicone oil has a viscosity of about 20 to 12,500.

11. The method of claim 1 wherein the concentration of said gelling agent in said lubricant is about 0.01 to 2.0% by weight.

12. The method of claim 1 wherein said dissolving step is performed at a temperature of about 100° to 300° C.

13. The method of claim 1 wherein said dissolving step is performed by dipping said article into said composition.

14. A method for lubricating an article comprising:
a) dissolving a dibenzylidene sorbitol in a silicone oil at a temperature which gives a homogeneous liquid composition;

b) applying said liquid composition to a surface of an article to give a coated article; and c) cooling said coated article to a temperature at which said composition gels on said article.

15. A method for lubricating an article comprising applying a liquid lubricating composition including a lubricant and a gelling agent selected from the group consisting of an ether of a polyhydroxy compound and a fatty acid salt to the surface of an article and causing said composition to cool and gel on said surface.

* * * * *